(12) United States Patent
Shi

(10) Patent No.: US 8,349,618 B2
(45) Date of Patent: *Jan. 8, 2013

(54) DIAGNOSTIC DEVICES

(75) Inventor: Qinwei Shi, Richmond Hill (CA)

(73) Assignee: ZBX Corporation, Toronto, ON (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/952,588

(22) Filed: Nov. 23, 2010

(65) Prior Publication Data

US 2011/0189791 A1 Aug. 4, 2011

Related U.S. Application Data

(63) Continuation of application No. 10/681,639, filed on Oct. 8, 2003, now Pat. No. 7,883,899.

(60) Provisional application No. 60/417,794, filed on Oct. 11, 2002.

(51) Int. Cl.
*G01N 21/77* (2006.01)

(52) U.S. Cl. ........ 436/169; 436/164; 436/518; 436/528; 436/529; 435/7.1; 435/283.1; 435/287.2; 435/287.9; 435/287.7; 422/68.1

(58) Field of Classification Search .................. 436/164, 436/169, 172, 528, 529, 530, 532; 435/7.1, 435/283.1, 287.2, 287.7, 287.9, 288.7; 422/68.1, 422/82.05
See application file for complete search history.

(56) References Cited

U.S. PATENT DOCUMENTS

| | | | |
|---|---|---|---|
| 4,703,017 A | 10/1987 | Campbell et al. | |
| 4,774,192 A | 9/1988 | Terminiello et al. | |
| 4,839,297 A | 6/1989 | Freitag et al. | |
| 4,861,711 A | 8/1989 | Friesen et al. | |
| 4,960,691 A | 10/1990 | Gordon | |
| 5,075,078 A | 12/1991 | Osikowicz et al. | |
| 5,110,724 A | 5/1992 | Hewett | |
| 5,120,643 A | 6/1992 | Ching et al. | |
| 5,135,716 A | 8/1992 | Thakore | |
| 5,271,895 A * | 12/1993 | McCroskey et al. | 422/408 |
| 5,411,858 A * | 5/1995 | McGeehan et al. | 435/4 |
| 5,559,041 A * | 9/1996 | Kang et al. | 436/518 |
| 5,591,645 A | 1/1997 | Rosenstein | |
| 5,622,871 A | 4/1997 | May et al. | |
| 5,654,162 A | 8/1997 | Guire et al. | |
| 5,656,503 A | 8/1997 | May et al. | |
| 5,714,389 A | 2/1998 | Charlton et al. | |
| 5,989,921 A | 11/1999 | Charlton et al. | |
| 6,001,307 A * | 12/1999 | Naka et al. | 422/81 |
| 6,020,147 A | 2/2000 | Guire et al. | |
| 6,104,484 A * | 8/2000 | Nagata et al. | 356/246 |
| 6,156,271 A | 12/2000 | May | |
| 6,171,870 B1 | 1/2001 | Freitag | |
| 6,187,598 B1 | 2/2001 | May et al. | |
| 6,214,629 B1 | 4/2001 | Freitag et al. | |
| 6,228,660 B1 | 5/2001 | May et al. | |
| 6,258,229 B1 * | 7/2001 | Winarta et al. | 204/403.04 |
| 6,300,141 B1 * | 10/2001 | Segal et al. | 435/287.1 |
| 6,319,676 B1 | 11/2001 | Nazareth et al. | |
| 6,352,862 B1 | 3/2002 | Davis et al. | |
| 6,410,341 B1 | 6/2002 | Freitag et al. | |
| 6,451,619 B1 * | 9/2002 | Catt et al. | 436/514 |
| 6,485,982 B1 | 11/2002 | Charlton | |

(Continued)

*Primary Examiner* — Melanie J Yu

(74) *Attorney, Agent, or Firm* — Sim & McBurney

(57) ABSTRACT

The present invention relates to analytical methods, platforms, and devices for the rapid and efficient immunochromatic determination of one or more components in fluid samples.

20 Claims, 3 Drawing Sheets

U.S. PATENT DOCUMENTS

| | | |
|---|---|---|
| 6,534,320 B2 | 3/2003 | Ching et al. |
| 6,612,111 B1 * | 9/2003 | Hodges et al. ............... 60/583 |
| 6,723,500 B2 * | 4/2004 | Yu ............................ 435/4 |
| 6,740,293 B1 * | 5/2004 | Deng ......................... 422/412 |
| 6,991,912 B2 * | 1/2006 | Feistel ....................... 435/7.92 |
| 7,238,534 B1 * | 7/2007 | Zimmer ..................... 436/169 |

* cited by examiner

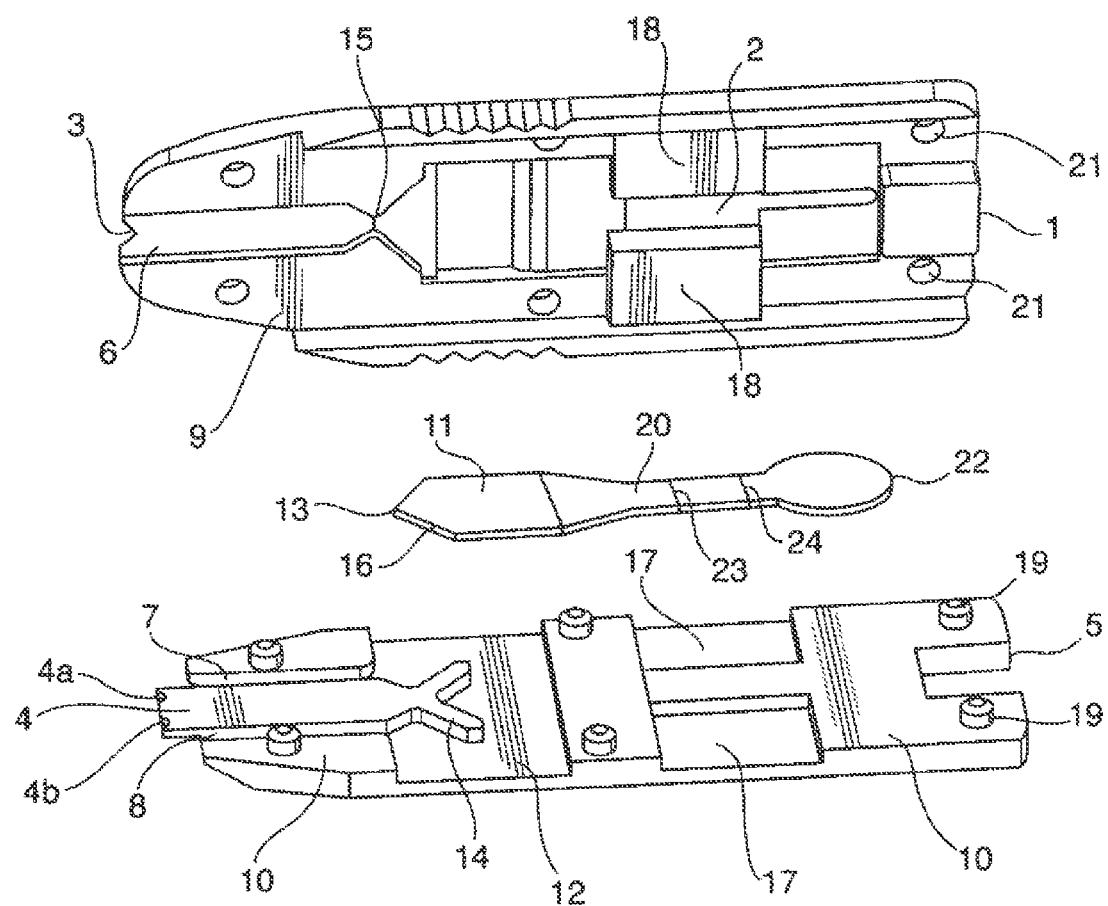

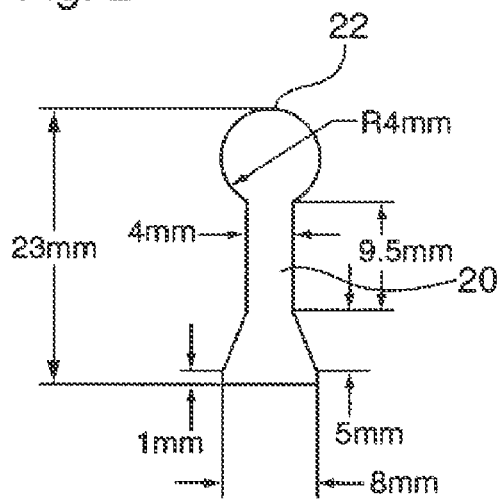
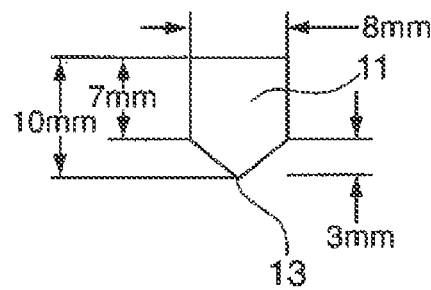
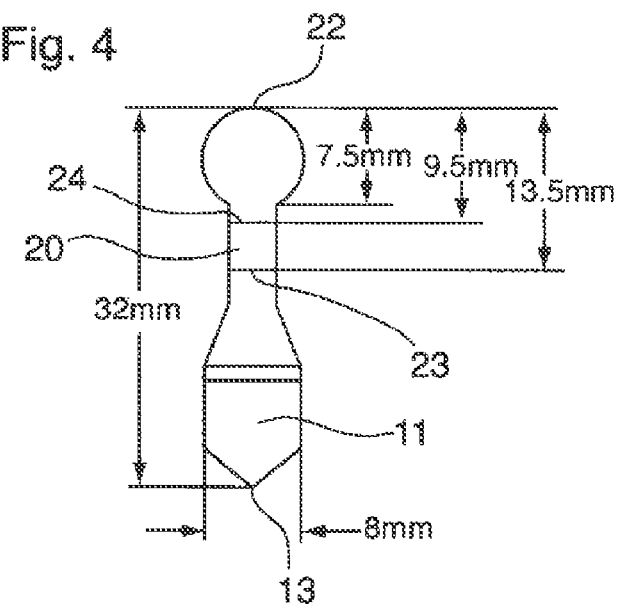

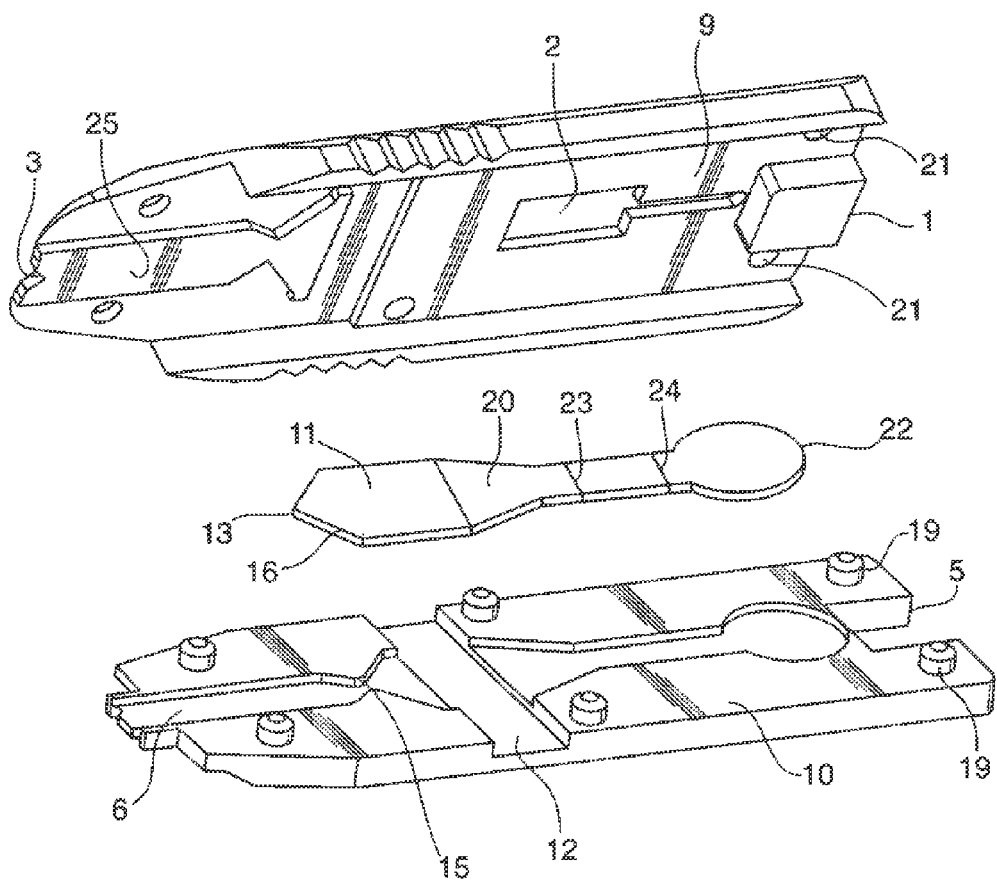

DIAGNOSTIC DEVICES

CROSS-REFERENCE TO RELATED APPLICATIONS

This application claims the benefit of U.S. Provisional Patent Application 60/417,794 having a filing date of Oct. 11, 2002, the entire contents of which are hereby incorporated by reference.

BACKGROUND OF THE INVENTION

This invention is concerned with platforms, devices and methods useful for analytical assays in fluid samples. It is especially concerned with determining the presence of one or more analytes in small volumes of whole blood, although it is not so limited.

Many immunoassay procedures have now been developed which utilize reactions taking place on dry porous carriers such as nitrocellulose membranes through which samples to be analyzed flow by capillary action, the reaction products being detectable either visually or with an instrument such as a reflectometer or fluorometer. While not so limited, these procedures often involve antigen/antibody reactions in which one member of the reactive pair is labeled with a detectable label. Typically, the label is an enzyme label or a particulate direct label, for instance sol labels such as gold. The art is well aware of many useful labels and their methods of operation.

Typical immunochromatographic devices of this nature are described in several United States and foreign patents including U.S. Pat. Nos. 4,703,017; 4,774,192; 4,839,297; 4,861,711; 4,960,691; 5,075,078; 5,110,724; 5,120,643; 5,135,716; 5,591,645; 5,622,871; 5,654,162; 5,656,503; 5,714,389; 5,989,921; 6,020,147; 6,156,271; 6,171,870; 6,187,598; 6,214,629; 6,228,660; 6,319,676; 6,352,862; 6,410,341; 6,485,982; and 6,534,320.

These patents generally describe devices that are composed of two basic parts: a dry porous carrier through which a fluid moves by capillary action and reactions determinative of the analyte take place; a casing formed with sample application means that supports the dry porous carrier and may contain a window to facilitate viewing of the results. Sample volume is typically measured before it is applied to the dry porous carrier.

These representative devices have permitted major diagnostic advances in the medical and veterinarian fields. However, some of them are deficient because they are expensive to manufacture, not easy to use or do not perform with the desired speed. None of them have proved capable of performing an immunoassay on small volume samples typically obtainable from a finger puncture without adding extra solution. The devices of this invention alleviate those problems because they are easy to manufacture and even in the hands of a novice or unskilled personnel will provide the required information rapidly and efficiently utilizing as little as one drop of sample. The devices of this invention also incorporate mechanisms to ensure that a minimum sample volume is present before test begins and the minimum sample volume is maintained during the testing process.

The products and procedures of this invention and their disclosed modifications can be utilized for many diagnostic purposes as well as for following the course of mammalian diseases and therapeutic treatments. A particular advantage is that the products and methods are applicable to small volumes of whole blood such as can be obtained from a simple finger puncture.

The invention is applicable to substantially any field in which a ligand or analyte is detected or quantified by antigen/antibody or equivalent reactions.

Analytes which may be detected in accordance with this invention include, for example, those indicative of pregnancy, ovulation, cancers such as prostate cancer and cardiovascular events. The analytes include for example hCG (human chorionic gonaditropin), LH (luteinizing hormones), PSA (protein specific antigen), myoglobin, troponins, and creatinine kinase MB.

Additional applications of the invention include recognition of analytes associated with viral infections such as hepatitis and bacterial infections such as *Helicobacter pylori* responsible for gastrointestinal ulcers as well as infections caused by *Salmonella* genus and such gram positive bacteria as *Bacillus anthracis, S. pyrogenes, S. pneumoniae* and *E. faecalis.*

As the description of the invention proceeds, it will be apparent that in addition to its utility for the assay of small sample volumes, another very important advantage is its applicability to immunoassay and non-immunoassay formats requiring the separation of red blood cells from plasma through fluid pathways.

The facility with which the devices may be employed makes it possible for their use by untrained personnel at home or in a doctor's office as well as for rapid determinations in an ambulance, emergency room, urgent care centre and laboratory.

GLOSSARY

The general meaning of the terms employed in the description of this invention are as follows.

Platform is a combination of upper and lower layers which may be opaque, translucent or transparent and are formed to contain and position a dry porous carrier construction. The layers are constructed and assembled to form a platform flow channel which in a cooperative relationship with the carrier form a flow through channel thereby permitting a given volume of liquid sample applied at the upstream end of the platform to flow to the distal end of the carrier by capillary action. In the devices of this invention, they are generally prepared from a rigid plastic with hydrophilic surfaces such as an acrylic polymer by standard, well known procedures including stamping, moulding, machining and equivalent processes.

Dry porous carrier and dry porous carrier layer refer to a porous material supported in the platform through which a liquid sample flows by capillary action. Such products are often referred to as membranes. They are the principal site where analytical reactions take place.

Device is the operative combination of platform and dry porous material useful for qualitative or quantitative determination of one or more components such as analytes or other ligands in a liquid sample.

Analytes are substances in or released into body fluids indicative of physiological or pathological conditions. They include, for example, cardiac analytes which are proteins released from myocardial cells into circulation due to deterioration of cardiac tissue, hormones indicative of pregnancy, glucose used to monitor a diabetic condition and various proteins or toxins resulting from infections.

Top or bottom layers are the upper and lower layers in the platform which are configured to hold a dry porous carrier and in cooperation therewith form a flow through channel upstream of the membrane and providing a pathway for a liquid sample to be tested.

Antigen is a large molecule or a hapten linked to a large molecule which, in a mammal, induces the production of an antibody. The devices of this invention are useful for determining the presence of antigens or antibodies in a fluid. They are especially useful for analyzing body fluids particularly whole blood. Antigens are often referred to as "analytes" since they are characteristic of specific physiological or pathological conditions such as pregnancy, infections, cancer or cardiac conditions.

Channel is any formed conduit or pathway through which the fluid sample under analysis flows in an analytical test device. In the products of this invention, the channels are formed by the cooperative arrangement and configuration of the adjacent surfaces of the upper and lower layers and the dry porous carriers. For convenience, in the description of this invention, a channel in the platform is referred to as a platform channel, and a dry porous carrier sometimes is referred to as a membrane channel. Together they form a flow through channel.

Rapid means that a detectable product forms within a sufficiently short period of time, e.g. within about 2 to about 10 minutes, to permit the user to draw meaningful and useful conclusions.

Efficient means that a detectable product can be formed with a low volume of fluid, e.g. one or a few drops of whole blood (from about 10 ul to about 50 ul), utilizing small quantities of reagents even when an analyte or other ligand is present in very low concentration as is usually the case with many analytes such as the cardiac analyte Troponin I.

Detecting reagent is a material, often an antibody to the analyte which is to be detected in the liquid sample. It is typically releasably bound to the dry porous carrier at or downstream of the application point for the liquid sample. For most immunochemical analyses, it is labeled with a detectable label such as colloidal gold and forms a complex with the analyte to be determined.

Capture reagent is a material, often a second antibody to the analyte which is to be detected in the liquid sample. It is fixed to the carrier downstream of the detecting reagent. It reacts with and concentrates the complex on the carrier to form a product which is visible to the naked eye or readable with the aid of a suitable instrument.

SUMMARY OF THE INVENTION

The invention provides design principles and devices, each device comprising a platform formed to receive and measure a low volume liquid sample for analysis and to encompass a dry porous carrier on which reactions take place, which permit the user to detect one or more components in the sample. In the methods of operation, the sample is applied to the platform flow channel and flows by capillary action towards the downstream or distal end of the carrier once enough sample is received in the platform channel. In the course of its flow in the dry porous carrier, the sample first encounters a detection reagent dried on/in the upstream section of the carrier. For the detection of antigenic analytes, the detection reagent is typically one or more antibodies, labeled with a detectable label. Each antibody reacts with an epitope on the analyte. The upstream section of the carrier may be a plasma separator material if the sample is whole blood.

The detecting reagent is releasably bound to the carrier membrane. As a result of the contact with the sample, an antigen/antibody reaction takes place to form a complex in the liquid sample and flows downstream by capillary action until it encounters a fixed capture reagent, typically a second antibody which reacts with different epitope[s] on the analyte.

The reaction with the fixed capture reagent concentrates the complex to form a fixed line which is visible to the naked eye or with appropriate instrumentation.

The devices of the invention are applicable to a wide variety of diagnostic procedures, especially those which utilize whole blood as the sample.

Amongst the many advantages of the devices of this invention are that overloading of the device with the sample does not affect the test results and underloading of the device with the sample can not produce a result. In addition, they are easy to manufacture, easy to use, utilize small volumes of sample and provide rapid results. For whole blood sample, they do not require sample processing and separate sample collection or measuring and transfer devices. No additional solution is required to use the device. The sample itself is all that is needed to achieve the desired results. A particular advantage is that the devices of the invention comprise three separate elements, the platform, the dry porous carrier and the combination of the two to form the detection device. Each element may be separately manufactured.

The devices of the invention are especially useful for the analysis of whole blood taken from a finger puncture for the presence of analytes which may be the result of a myocardial damage. These analytes include troponins, brain natriuretic peptide, and others. It will be recognized that the use of the devices is not limited to these specific analytes or, indeed, to whole blood but is equally applicable to a host of other diagnostic procedures.

BRIEF DESCRIPTION OF THE DRAWINGS

The invention will be better understood by reference to the accompanying drawings which illustrate representative embodiments of the invention in which:

FIG. 1 is an exploded view illustrating the various parts of one specific device of the invention;

FIGS. 2, 3, and 4 show a preferred membrane construction of the invention with an indication of the dimensions and configuration of the detection and capture membranes which may be used in the platform of FIG. 1. The dimensions are merely exemplary since variations are possible depending inter alia upon the type of membrane, sample, and the sensitivity required. The specific dimensions of the membranes shown in FIGS. 2, 3 and 4 are established to analyze one drop of whole blood (about 35 ul) in less than 10 minutes; and FIG. 5 illustrates another embodiment of the invention in which the platform flow channel is formed with an indent in the top surface of the lower layer.

DETAILED DESCRIPTION OF THE INVENTION

According to the present invention, a rapid chromatographic assay device utilizing a small volume of sample, such as one drop of whole blood typically obtainable from a finger puncture, is provided. This device obviates some of the deficiencies of the prior art devices, such as analyses of small volumes of whole blood samples. Other deficiencies which are eliminated include the requirement of separate sample collection, volume measurement and transfer devices, requirement of more than one drop (>35 μL) of sample and requirement of additional solutions to facilitate adequate sample flow.

The device incorporates the following design principles: A sample flow channel is formed between the upper and lower layers of the platform each having a hydrophilic surface, with dimensions that allow capillary flow. The platform flow channel is in communication with the dry porous carrier and has a volume equal or greater than the sample volume requirement for the test. In preferred devices, the upstream end of the platform flow channel may include notches adjacent to the platform flow channel entry point to facilitate sample application. For example, as shown in FIGS. 1 and 5 small notches provide alternate sample entry to the platform flow channel when the main opening is blocked as a result of pressing the device against a fingertip. The downstream end of the platform flow channel narrows to promote increased capillary force and uniform flow of the sample front into the dry porous carrier. Open areas are designed around the platform flow channel to inhibit sample leaking into spaces between upper and lower layers if the platform flow channel is not sealed by means such as adhesives or welding. Narrow surface-to-surface overlapping areas between the upper and lower layers of the platform are designed around the platform flow channel to create a greater capillary force so that the overlapping areas will be filled first with the sample before the platform flow channel is filled. This serves as a sealing mechanism to prevent air leaking into platform flow channel already filled with sample, which could impede sample flow. An important feature of the platform is that sample enters the dry porous carrier from the edges as opposed to the top. In the prior art devices, sample is applied to the top of the dry porous carrier and due to the outward spreading nature of liquids, there is always wasted sample that travels contrary to the direction of the main flow. This loss is significant for devices that are intended for small sample volumes.

The size of the dry porous carrier is designed based on the test volume. The length of the dry porous carrier is designed based on the test time requirements. For whole blood samples, two types of material for the dry porous carrier are preferred. The first material, a plasma separator at the upstream section of the dry porous carrier has a liquid capacity to retain the red blood cell fraction of the sample. The second material, the site of the immobilized capture reagent has a liquid capacity approximately equal to the volume of plasma in the sample. The liquid capacity of and the sample flow rate within the dry porous carrier can be determined by a few simple observations.

For small sample volumes, it may be desirable to minimize evaporation of any significant portion of the sample therefore to use of a vapour barrier on the surfaces of the dry porous carrier is preferred.

One embodiment of the present invention designed for a single drop of whole blood sample is shown in FIG. 1.

FIG. 1 includes a bottom view of the upper layer 1 of a platform having an aperture or window 2 through which the dry porous carrier structure and the reactions which take place on or in it can be viewed. The window is optional if the top layer of the platform is transparent or translucent. It is, of course necessary if the platform is opaque.

Indent 3 in cooperation with support 4 in the lower layer 5 having notches 4a and 4b provides additional entry means for the sample.

The entry means in the device shown is in registry with a platform flow channel formed to include indent 6 in the bottom surface 9 of the upper layer 1. There are open areas 7 and 8 where the bottom surface 9 of the upper layer 1 comes into contact with the top surface 10 of the lower layer 5. These open areas inhibit flow of the sample from the platform flow channel into the space between the two surfaces. The open areas 7 and 8 extend into the area 12 to prevent sample from flowing out of dry porous carrier 11 and 20 into the space between the two surfaces 9 and 10.

The platform flow channel terminates at the apex 13 of the upstream end of dry porous carrier 11. This section of dry porous carrier 11 is supported by a Y-shaped protrusion 14 extending from the top surface 10 of lower layer 5. It will be noted that the downstream end of the platform flow channel is constricted at 15 so that the sample flows uniformly into the dry porous carrier 11 at the apex 13. There is also a surface-to-surface contact between the dry porous carrier edge 16 and sidewalls of the widening area downstream of the constriction 15 of upper layer 1. Since this space is even narrower than constriction 15, it promptly fills with sample resulting in a more uniform sample entry into dry porous carrier 11. The dry porous carrier has greater capillary force than that of the platform flow channel causing all sample in the platform flow channel to move into the dry porous carrier. This interplay of capillary forces is a major factor that permits the devices of the invention to start the diagnostic reaction only if enough blood is received, thereby avoiding false results caused by insufficient sample volume.

There are indents 17 in the top surface 10 of lower layer 5 and rectangular protrusions 18 from the bottom surface 9 of the upper layer 1. These features serve two purposes. One is to assist in holding the two layers together. The other is to hold the dry porous carrier firmly in position when the device is completely assembled.

To further assist in holding the two layers together to form a platform there are cylindrical pillars 19 in the top surface of the lower layer 10 which register with cylindrical indents 21 in the bottom surface 9 of the upper layer 1.

As will be apparent from a consideration of the dimensions shown in FIGS. 2, 3 and 4, the apex 13 of detection membrane 11 contacts the downstream end of the platform flow channel. The downstream end of detection membrane 11 slightly overlaps the upstream end of capture membrane 20. Thus there is formed a flow through channel permitting the sample to flow from platform flow channel to detection membrane 11 to the closed end 22 of capture membrane 20. The total absorption volume of capture membrane 20 and detection membrane 11 is substantially equal to the desired volume for the test. Accordingly, when the fluid sample has completed its capillary flow to the end of membrane 20 the platform flow channel is substantially empty. This arrangement serves as a control to ensure that enough sample volume is present before the diagnostic reaction begins.

The design shown in the FIGS. 2, 3 and 4 is intended for the detection of an analyte in a drop of whole blood in less than 10 minutes. It illustrates a preferred structure in which there are two membranes, an upstream detection and plasma separation membrane 11 and a downstream capture membrane 20.

FIG. 5 illustrates another structure within the scope of the invention. The device illustrated is similar to the device of FIG. 1, except that the platform flow channel is formed in the top surface 10 of the lower layer 5. In the figure, those parts of the device which are equivalent to those of the earlier figure are identified by the same reference numerals. However, the platform flow channel is formed by protrusion 25 which registers with an indent 6 in the top surface 10 of lower layer 5 to form platform flow channel. The platform flow channel can also be formed by registry of indents in the bottom surface of the top layer and the top surface of the bottom layer. This variation of the platform will be readily obvious to the skilled artisan and is not shown.

The detection membrane 11 performs two functions. It performs a filtration function to separate plasma from a fluid stream of whole blood. It also serves as the site for the deposit of a detecting reactant for the analyte, for example a labeled antibody to form an antigen/antibody complex. Although it is not preferred, the detecting reactant could also be placed on the capture membrane 20 or in the platform flow channel.

The presently preferred material for the detection membrane 11 is a glass fibre product such as the Whatman F487-14 membrane (available from Whatman, Inc. at Clifton, N.J.). Other useful membrane materials are synthetic fibre membranes available from Pall Corporation of Long Island, N.Y. and the polyethersulfone and pyrrolidone products obtainable from Spectral Diagnostics of Toronto, Canada.

The immunochemical methods employed in the practice of this invention are the same as employed with previously known devices except that because of the unique structure of the platform, it rules out false results by over filling or under filling the device. Additionally, the sample may be small and will traverse the device at a rapid rate. Thus, the method of placing the reagent on or in the membranes is similar to previous procedures. The passage of the sample through the membranes is downstream from an application area to a point of analyte capture where there is a detectable result. Stabilizing reagents, and transport facilitating reagents may be utilized in accordance with standard practice, although their use is optional.

To facilitate handling, the membrane may be backed with a backing tape (not shown), typically a polystyrene tape with an appropriate adhesive which will not migrate into the membrane. One such tape is Super White Polystyrene tape available from G & L of San Jose, Calif.

There may also be a transparent cover tape (not shown) for the membrane to limit loss of sample from the membrane by evaporation. Typically, these cover tapes are thin polyester films about 50 um thick with a non-migrating adhesive. One such film is ARcare clear polyester available from Adhesives Research, Inc. of Glen Rock, Pa.

As is standard with these types of analyses, the result of the reaction is obtained by observing the capture line 23 (FIG. 4) and an optional control line 24 (FIG. 4). In immunochemical analyses, the detectable capture line 23 is the site of the formation of the labeled antibody/analyte/fixed antibody product. The control line 24 may contain any reactant which will form a visible product with a component of the sample or with a mobile reagent formed or utilized in the analytical reaction.

To achieve the advantages of this invention, especially the speed of operations, it is important to select the dimensions, shape and placement of membranes 11 and 20.

In order to obtain rapid movement of the sample through the two membranes in the embodiments illustrated and yet retain the capture and control lines sufficiently separate to be visible through the window 2, the capture membrane 20 is shaped with a narrow mid portion and a circular downstream portion. The dimensions of the membranes are selected so that the total absorption volume of the capture and detection membranes is substantially equal to the required volume of the sample.

This latter feature could also be achieved by forming the membranes in the shape of a longer rectangle. However, the resulting time to complete the test would be undesirably extended. It could also be achieved by shortening the rectangle and increasing its crosswise dimensions. This would decrease the time to complete the test but the capture and control lines would necessarily be too close together to be easily distinguishable through window 2. This construction may also reduce the sensitivity of the test.

Test completion is indicated by the sample flow to the end of 22 of the capture membrane 20 and may be visibly evident in the window 2 in the upper layer 1. Thus, a timing device is only optional to determine test completion.

Any of a variety of labels available to the skilled artisan may be utilized in the devices of this invention. Metal and enzyme labels are preferred. Metal labels are especially preferred due to their remarkable sensitivity. Amongst the metals, gold is most preferred principally because its characteristics are so well understood.

The preferred particle size for gold labeled antibodies employed in the invention is from about 20 to 65 nm, although appreciable variation can be tolerated depending on well understood factors such as the analytical sensitivity of the test and the affinity of the reactants.

For the analysis of whole blood, the capture membrane 20 is preferably formed from nitrocellulose or equivalent product. It is available from Whatman.

Many apparent variations of this invention are possible without departing from its spirit and scope. For example, the platform flow channel can be formed with indent in either the top or lower layer as described above.

While the various embodiments of the invention have been described principally as applied to a sandwich assay, it will be apparent to the skilled artisan that the devices and principles of this invention can readily be adapted to competitive or other assays.

All of the platforms, membrane and devices of this invention are prepared by conventional, well know procedures from materials which are readily available commercially.

In typical applications of this invention to a whole blood sample, a detection membrane is impregnated with a releasably bound labeled antibody which will react with an epitope on the analyte. These analytes may be, for instance: hCG; Myoglobin; C Reactive Protein; L H; Troponin I or T; ApoB 100; PSA; Creatinine Kinase MB; and Brain Natriuretic Peptide. The second or capture membrane is the site of an impregnated, immobile second antibody which reacts with another epitope on the analyte. Downstream of the second antibody there is an impregnated control reagent which will react to indicate that the test is valid.

The whole blood sample is added to the device through the platform flow channel and flows into and through the detection membrane. In the detection membrane, the red blood cells are removed from the sample by filtration. The sample contacts the first antibody which is labeled to result in the formation of a labeled antibody/analyte complex in liquid sample and flows downstream to the capture membrane. In the capture membrane, the complex reacts with the capture antibody to form a labeled antibody/analyte/capture antibody product which is concentrated at the capture line. The plasma continues to flow past the capture line to a control site downstream of the capture line. At the control site there is a reaction which indicates that the test is valid by the appearance of a control line.

With the benefit of the teachings of this disclosure, the skilled artisan can readily adapt any number of well-known methods, and reagents to detect analytes or other ligands utilizing the novel devices of this invention.

The present invention is further illustrated by the following Example 1, but this Example should not be construed as limiting the scope of the invention.

EXAMPLE 1

A human chorionic gonadotropin (hCG) test device using one drop of whole blood sample is prepared according to current invention. Platform and dry porous carrier were constructed as shown in FIGS. 1 to 4.

Nitrocellulose capture membranes (Whatman) were impregnated with both control and capture solutions using a conventional liquid dispenser. The control solution contained 1 mg/mL of goat anti-mouse IgG polyclonal antibodies obtained from Arista Biologicals. The capture solution contained 2 mg/mL of affinity purified goat anti-human hCG alpha chain polyclonal antibodies (also from Arista Biologicals). The impregnated membranes were incubated at 37° C. for 30 minutes to immobilize the antibodies. Gold conjugate, prepared from 40 nm gold particles and a monoclonal antibody specific to human hCG beta chain, was purchased from Arista Biologicals and had a final optical density 3.0 at 540 nm. The detection membrane, a plasma separator (Whatman), was sprayed with colloidal gold conjugate solution and then freeze dried to remove water. The test strip was covered by a 25 um thick transparent polyester tape (Adhesive Research) and supported by polystyrene tape available from G & L Precision Die Cutting, Inc. The shape of the test strip was produced using a die-cutting tool. Testing of the assembled device using 35 uL of blood demonstrated excellent plasma separation and sample flow. The testing procedure took approximately 6 minutes to complete. A sensitivity of 20 mIU hCG/mL was observed.

It is appreciated by those skilled in the art that various changes and modifications can be made to the illustrated embodiments and description herein without departing from the spirit of the invention. All such modifications and changes are intended to be covered by the appended claims.

What is claimed is:

1. A platform comprising one or more dry porous membranes for detecting at least one component in a liquid sample, wherein:
   the platform is formed from top and bottom layers comprising respective top and bottom hydrophilic surfaces that are brought into fixed face to face contact to enclose and position the membranes and form a platform flow channel and a sample application means; and
   the platform flow channel is in fluid communication with the membranes and is configured to promote increased capillary force and uniform flow of the sample by capillary action in a continuous pathway from the sample application means through the platform flow channel and then to an edge of an upstream end of the membranes towards the distal end of said membranes.

2. The platform according to claim 1 wherein the platform flow channel has an indent in the bottom surface of the top layer.

3. The platform according to claim 1 in which the platform flow channel is formed in the top surface of the bottom layer.

4. The platform according to claim 1 in which the platform flow channel is formed with indents in the top surface of the bottom layer and in the bottom surface of the top layer.

5. The platform according to claim 1 further comprising a window in the top layer for observing the results of a reaction which takes place in the membrane.

6. The platform according to claim 1 wherein the membrane contains one or more reagent[s] for detecting one or more analyte[s].

7. The platform according to claim 6 wherein the analyte is selected from the group consisting of hCG, LH, PSA, Myoglobin, Troponin I, Troponin T, Creatinine Kinase MB, C Reactive Protein, ApoB 100, and Brain Natriuretic Peptide.

8. A platform comprising a detection membrane and a capture membrane for rapid and efficient detection of one or more components in a whole blood sample, wherein:
   the detection membrane is constructed to filter substantially all of the red blood cells from the sample and contains a mobile labeled detecting reagent which will react with the one or more components to form a reaction product which moves downstream in the detection membrane;
   the capture membrane is downstream of the detection membrane and contains a fixed, immobile capture reagent which reacts with and concentrates the reaction product at a capture line, the downstream end of the detection membrane overlapping the upstream end of the capture membrane;
   the platform is formed from top and bottom layers comprising respective top and bottom hydrophilic surfaces that are brought into fixed face to face contact to enclose and position the membranes and form a platform flow channel and a sample application means; and
   the platform flow channel is in fluid communication with the membranes and is configured to promote increased capillary force and uniform flow of the sample by capillary action in a continuous pathway from the sample application means through the platform flow channel and then to an edge of the upstream end of the detection membrane towards the downstream end of the capture membrane.

9. The platform according to claim 8 wherein the platform flow channel has an indent in the bottom surface of the top layer.

10. The platform according to claim 8 in which the platform flow channel is formed with an indent in the top surface of the bottom layer.

11. The platform according to claim 8 in which the platform flow channel is formed with indents in the top surface of the bottom layer and bottom surface of the top layer.

12. The platform according to claim 8 further comprising a window in the top layer for observation of the results of a reaction which takes place in the capture membrane.

13. The platform according to claim 8 wherein the detection membrane contains one or more reagent[s] for detecting one or more analyte[s].

14. The platform according to claim 13 wherein the analyte is selected from the group consisting of hCG, LH, PSA, Myoglobin, Troponin I, Creatinine Kinase MB, C Reactive Protein, ApoB 100, and Brain Natriuretic Peptide.

15. The platform according to claim 8 wherein the detecting membrane is a glass fibre membrane and the capture membrane is a nitrocellulose membrane.

16. The platform according to claim 8 wherein the membranes are covered with a transparent cover layer.

17. The platform of claim 1, wherein said top and bottom layers further comprise open areas to inhibit the flow of the sample from said platform flow channel into space between the surfaces of said top and bottom layers.

18. The platform of claim 1, wherein said top surface of the bottom layer further comprises indents that mate with rectangular protrusions in said bottom surface of the top layer.

19. The platform of claim 1, wherein said top surface of the bottom layer further comprises cylindrical pillars that register with cylindrical indents in said bottom surface of the top layer.

20. A method for detecting at least one component in a liquid sample, the method comprising:
   applying the sample to the platform of claim 1 such that the sample flows in a continuous pathway from the upstream sample application means through the platform flow channel and then to an edge of an upstream end of the membranes towards the distal end of said membranes; and
   detecting the presence or absence of the component by reading a result near the distal end of said membranes.

* * * * *